United States Patent
Pascaly et al.

(10) Patent No.: US 7,626,006 B2
(45) Date of Patent: Dec. 1, 2009

(54) PROCESS FOR PREPARING ALKYLGLYCOSIDES

(75) Inventors: Matthias Pascaly, Munster (DE); Burghard Gruning, Essen (DE); Dietrich Maass, Altenberge (DE); Christian Weitemeyer, Essen (DE)

(73) Assignee: Goldschmidt GmbH, Essen (DE)

( * ) Notice: Subject to any disclaimer, the term of this patent is extended or adjusted under 35 U.S.C. 154(b) by 605 days.

(21) Appl. No.: 11/113,750

(22) Filed: Apr. 25, 2005

(65) Prior Publication Data

US 2005/0261484 A1 Nov. 24, 2005

(30) Foreign Application Priority Data

May 22, 2004 (DE) .................. 10 2004 025 195

(51) Int. Cl.
C07H 15/04 (2006.01)
(52) U.S. Cl. .................... 536/18.6; 536/120
(58) Field of Classification Search ............... 536/18.6, 536/120, 201
See application file for complete search history.

(56) References Cited

U.S. PATENT DOCUMENTS

| | | | |
|---|---|---|---|
| 2,276,621 A | 3/1942 | Langlois | |
| 3,375,243 A | 3/1968 | Nevin et al. | |
| 3,772,269 A | 11/1973 | Lew | |
| 4,465,828 A | 8/1984 | Rau et al. | |
| 4,898,934 A | 2/1990 | Lueders et al. | |
| 5,432,269 A | 7/1995 | Borsotti et al. | |
| 6,528,629 B2 * | 3/2003 | Rogers et al. | 536/18.5 |
| 2002/0099185 A1 | 7/2002 | Rogers et al. | |

FOREIGN PATENT DOCUMENTS

| | | |
|---|---|---|
| DE | 3611035 A1 | 10/1987 |
| EP | 0 725 144 A1 | 8/1996 |
| EP | 0 970 097 B1 | 4/2002 |
| FR | 1.114.382 | 9/1954 |
| JP | 6-92984 | 4/1994 |
| JP | 7-87992 | 4/1995 |
| JP | 8-67690 | 3/1996 |
| JP | 9-87294 | 3/1997 |

OTHER PUBLICATIONS

Clifford, T., Fundamnetals of Supercritical Fluids, 1998. 1-4.*
de Goede, Antonius T.J.W., et al., "Synthesis of Alkyl Fructosides", Starch/Starke (1995), vol. 47, pp. 233-237.

* cited by examiner

*Primary Examiner*—Shaojia Anna Jiang
*Assistant Examiner*—Ganapathy Krishnan
(74) *Attorney, Agent, or Firm*—Scully, Scott, Murphy & Presser, P.C.

(57) ABSTRACT

The invention relates to a process for preparing alkylpolyglycosides from monomeric glycosides, oligo- or polyglycosides and alcohols according to the general scheme $$(\text{Glyc-O})_z\text{H} + R^1\text{—OH} \rightarrow (\text{Glyc-O})_{z'}R^1$$

where
$z \geq 1$,
$z' \leq z$, preferably from 1 to 10,
(Glyc-O)— is a glycoside radical,
$R^1$ is a hydrocarbon radical which optionally contains multiple bonds and/or heteroatoms, which comprises carrying out the reaction under supercritical conditions with regard to the alcohol, preferably at pressures and temperatures which are at least 5% above the critical parameters, the alcohols serving both as the solvent and as reactants.

15 Claims, 1 Drawing Sheet

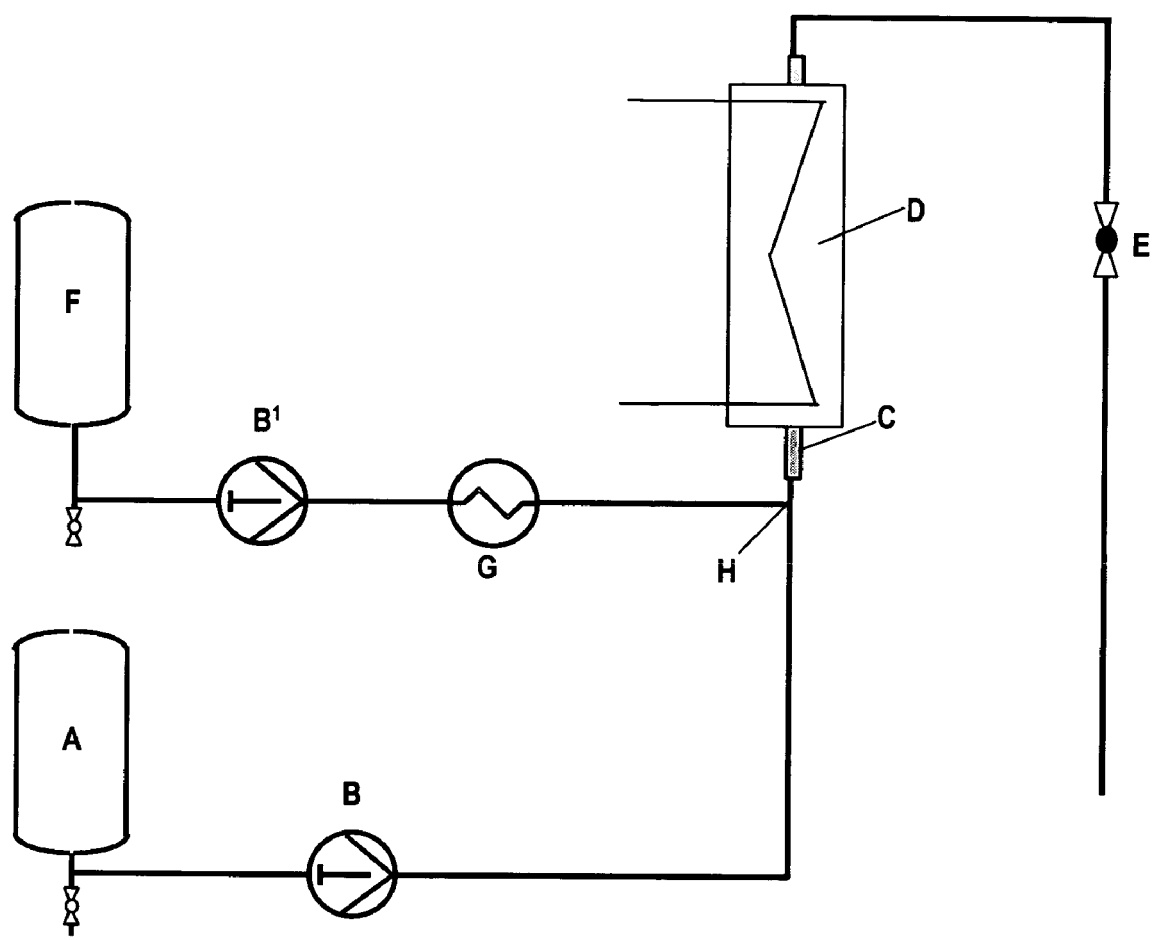
Figure

PROCESS FOR PREPARING ALKYLGLYCOSIDES

FIELD OF THE INVENTION

The present invention relates to alkylglycosides and more particularly to a method for preparing alkylglycosides from monomeric glycosides, oligo- or polyglycosides and an alcohol.

BACKGROUND OF THE INVENTION

Glycosides is the collective term for an extensive group of vegetable materials and synthetic compounds which are cleaved by boiling with water or dilute acids or under the action of glycosidases into one or more carbohydrates (mono- or oligosaccharides) and other compounds. The sugars are bonded by an oxygen atom in a glycosidic bond (generally an ether bond) to a hemiacetal carbon atom to give the full acetal. (Römpp Lexikon Chemie—Version 2.0, Stuttgart/New York: Georg Thieme Verlag 1999).

The monomer of the glycosides is usually a monosaccharide, for example, glucose (most frequently) or galactose, mannose, fructose, inter alia, hexoses or the pentoses arabinose, xylose, ribose; additionally, sugars also occur which are found exclusively in glycosides, for example, digitalose, cymarose, and etc. When the carbohydrate radical of a glycoside is a glucose, the derivative is known as a glucoside; analogously, the fructosides are glycosides with fructose as the sugar component, galactosides are glycosides with galactose as the sugar component. (Römpp Lexikon Chemie—Version 2.0, Stuttgart/New York: Georg Tneme Verlag 1999).

Methylglycosides are starting materials for the synthesis of alkylglycosides. These are full acetals which are prepared from sugar hemiacetals. Analogously, the corrpnding ketals are formed from the nonreducing sugars (lit.: A. T. J. W. de Goede, F. van Rantwijk, H. Van Bekkum, Starch/Starke 47 (1995) 233-237). The ketals are an extremely important substance class for the cosmetics industry. The most important compounds by far (possibly after further modifications) are typically used as nonionic surfactants with good foam properties, as emulsifiers or as thickeners. The advantages of these compounds are their low mucosa irritation potential and their biodegradability.

The classical synthesis of alkylglucosides is effected by reaction of sugars or carbohydrates with alcohols in the presence of an acidic catalyst (Fischer glycosidation; lit.: A. F. Bochkov, G. E. Zaikov: The Chemistry of the O-Glycosidic Bond, Pergamon Press, Oxford, 1979, 210 pp.). In order to enable a reaction of the mutually immiscible reactants, the mixture is kept at a high temperature for a long time and the water which forms is removed. Even the simple hydrolysis of a carbohydrate entails relatively drastic conditions resulting from use of 1 M sulfuric acid and 100° C. for several hours (this is the case for hexose-containing polysaccharides; lit.: Frieder W. Lichtentaler, in: Ullmann's Encyclopedia of Industrial Chemistry, "Carbohydrates"). In the course of this, however, partial decomposition of the sugars cannot be prevented. Generally, the product composition depends greatly upon the selected catalyst. In a two-stage synthesis, it is initially possible to prepare a glycoside having a short allyl chain which is subsequently exchanged for another alkyl radical by transacetalization in the presence of an acid.

Typical catalysts for the alkylation of glycosides are sulfuric acid and p-toluenesulfonic acid, as described, for example in U.S. Pat. Nos. 3,772,269 and 3,375,243. Such strong acids cause intense coloration of the product, which necessitates workup of the product. In addition, the use of mixed salts of a strong organic acid and a weak organic base is known (see, for instance, U.S. Pat. No. 5,432,269), but the products prepared in this way are also strongly colored and can contain free organic bases. Salts ofpolybasic carboxylic acids (see, for example, U.S. Pat. No. 4,898,934) and hydroxycarboxylic acids (see, for example, U.S. Pat. No. 4,465,828) are also used as catalysts. However, when the reaction mixture is concentrated, a colored product is unavoidably obtained as a result of the thermal stress in the presence of a concentrating acid. Therefore, a step for decolorization of the product (for example, with $H_2O_2$) has to follow in all cases.

The simplest and cheapest glycoside is methylglucoside (see formula II in scheme 1), whose preparation has been known for some time: see Römpp Chemie Lexikon, heading: α-methylglucoside: Preparation by the action of methanol on glucose in the presence of HCl or a cation exchanger. β-Methylglucoside is additionally formed.

Scheme 1:

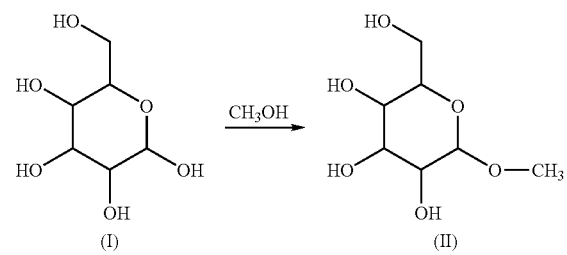

(I)  (II)

This synthesis is also described in numerous patents, see for example, U.S. Pat. No. 2,276,621 (publication date Mar. 17, 1942). The reaction is carried out in methanol as the alcoholic component and simultaneously the solvent, in the presence of a carbohydrate, for example starch. The catalysts used are inorganic acids, for example, sulfuric acid. The carbohydrate hydrolyzes to give glucose and methylglucoside is obtained in the presence of the catalyst.

JP-A-06-092984 describes the use of an immobilized catalyst system based on a cation exchanger resin for the preparation of methylglucoside, which is said to enable a preparation of only slightly colored products. Analogously thereto, the use of Amberlyst 15 is described in DE-A-3 611 035.

FR-1 114 382 describes the reaction of potato starch with methanol in the presence of HCl. A further reaction entails the addition of dilute sulfuric acid and subsequent decolorization.

One method for preparing alkylglycosides directly from oligo- or polyglycosides is, according to the prior art, possible only in a laborious process by hydrolytic cleavage (enzymatically, for example, with glycosidases, or chemically by acid catalysis) in the presence of a catalyst in alcohols.

When the above-mentioned customary methods are used, a multitude of by-products are obtained, and also the products tend to be intensely colored (mainly unreacted sugars), therefore further workup of the product becomes necessary.

The preparation of alkypolyglycosides is described, for example, in EP-B-0 970 097. For the formation of the full acetal, a monosaccharide is reacted at high temperature and standard pressure with an excess of alcohol in the presence of a mixture of sulfuric acid and sodium hydroxide or sodium carbonate as a catalyst. Even though neutralization of the reaction mixture by suitable selection of the catalyst mixture is not normally necessary, an addition of bases may be necessary in this case too. The alcohols used may be any monoor polyhydric primary or secondary alcohols. Enzymatic glycosidation is also known (JP-A-9087294, EP-A-725 144, JP-A-806 769 0, JP-A-708 799 2).

The reaction of very different sugars, for example, maltose, and even of polymeric nature, is also known. The acid catalyzed reaction of malto-oligosaccharides with alcohols or thiols is described in U.S. Patent Publication No. 2002/099185.

However, all of the prior art preparation processes are time-consuming batch syntheses of the corresponding alkylglycosides in which, owing to the harsh conditions to which the reactants are exposed over a long time, numerous by-products, which cause intensive coloration of the product, can be obtained.

There is still a need to provide a method for the simple and inexpensive synthesis of alkylglycosides, in which these products can be prepared in high space-time yields, continuously or batchwise, by direct reaction of sugars, oligo- or polyglycosides, as far as possible, without additions of catalysts or activators, in such a way that a further workup, for example with bleaches, is not required.

SUMMARY OF THE INVENTION

It has now been surprisingly found that, natural and unnatural glycosides, and also oligo- and polyglycosides, react at high pressures and high temperatures (both parameters at least have to attain the critical values of the alcohol) by reaction of the carbonyl group with the alcohol, which corresponds ultimately to a simple reaction of the hemiacetal to give a full acetal. It has also been found that polyglycosides can be cleaved under these conditions into their monomers, the glycosides, to form fullly acetalized monomers (cf scheme 1). Glycosides containing acid groups, for example, pectins, are also esterified under the conditions selected.

The present invention provides a process for preparing alkylpolyglycosides from monomeric glycosides, oligo- or polyglycosides and alcohols according to the general scheme

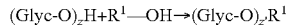

where
$z \geq 1$,
$z' \leq z$, preferably from 1 to 10,
(Glyc-O)— is a glycoside radical,
$R^1$ is a hydrocarbon radical which optionally contains multiple bonds and/or heteroatoms, which comprises carrying out the reaction under supercritical conditions with regard to the alcohol.

BRIEF DESCRIPTION OF THE DRAWINGS

The sole FIGURE of the present application is a schematic diagram of the process that can be used in the present invention for preparing allylglycosides. In this FIGURE, A is a vessel, B and B' are pumps, C is a reactor, D is a heater, E is a valve, F is the carrier stream reservoir, G is the carrier stream preheater, and H is the mixing point.

DETAILED DESCRIPTION OF THE INVENTION

As stated above, the present invention provides a simple and inexpensive method of preparing alkylglycosides from monomeric glycosides, oligo or polyglycosides and an alcohol. In the inventive reaction of monomeric glycosides, and oligo- and polyglycosides, the full acetals are obtained by reaction in supercritical alcohols according to the general scheme 2:

Scheme 2:

Reaction of a Polyglycoside with Alcohol

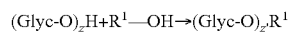

where
$z \geq 1$,
$z' \leq z$, preferably from 1 to 10,
$(\text{Glyc-O})_z\text{H}$ where $z=1$ are aldoses, for example, trioses, tetroses, pentoses, hexoses, in particular, erytirose, threose, ribose, arabinose, xylose, lyxose, allose, altrose, glucose, mannose, gulose, idose, galactose, fructose and glycoside derivatives, in particular, glucosamine, N-acetylglucosamine, rhamnose, fucose, 2-deoxy-D-erythropentose, glucuronic acid, galacturonic acid, adipose, hamamelose and tetraacylglucose,
$(\text{Glyc-O})_z\text{H}$ where $z>1$ are oligo- or polymers with the above-mentioned monomers, and are the same or different, i.e., oligo- or polyglycoside, in particular, sucrose, trehalose, raffinose, lactose, cellobiose, maltose, isomaltulose, lactulose, cyclodextrin, amylose, cellulose, chitin, starch, inulin, amylopectin, pectins, dextrans.

Particularly preferred starting compounds of the formula $(\text{Glyc-O})_z\text{H}$ are glucose and compounds thereof.

Suitable reactants and simultaneously solvents are, in principle, all alcohols. In the primary or secondary alcohols of the general formula $R^1$—OH which can be used in accordance with the invention,
$R^1$ is an optionally branched hydrocarbon radical, optionally containing double bonds, or a hydroxyalayl, alkyloxy radical having from 1 to 30 carbon atoms, in particular, from 1 to 18, preferably from 1 to 4, and the radical may also contain ali- or heterocyclic components, saturated, unsaturated or aromatic, having a ring size of from 3 to 10 atoms, preferably from 4 to 6 atoms, which may bear further saturated or unsaturated hydrocarbon substituents having from 1 to 30 carbon atoms, preferably from 1 to 18 carbon atoms, in particular $<C_{10}$ and more preferably $<C_5$, such as, methanol, ethanol, propanol.

Table 1 lists some compounds the can be used in the present invention by way of example.

Compounds of the formula II which are suitable for the process according to the invention are, in particular, alkanols, preferably methanol, ethanol, propanol, isopropanol, octanol, dodecanol, hexadecanol, octadecanol and 2-ethylhexanol, and also polyols, in particular ethylene glycol, diethylene glycol, polyethers, glycerol and trimethylolpropane. Amino alcohols may also be used, such as, ethanolamine, diethanolamine and triethanolamine, and aromatic alcohols, in particular, phenol, benzyl alcohol and catechol, and alicyclic alcohols, in particular, cyclopentanol and cyclohexanol, but also unsaturated alcohols such as hexenol, hexadecenol and octadecenol. It is also possible in the context of the present invention to use suitable alcohols in mixtures with one another, in which case it is, in some cases, sufficient when the supercritical conditions are attained for one of the alcohol components.

The reaction may optionally be carried out in the presence of suitable homogeneous and heterogeneous catalysts selected from the group of the protic acids, in particular, HCl, $H_2SO_4$, $H_3PO_4$, acetic acid, citric acid, or of the salts, in particular, $AlCl_3$, $LiClO4$, $LiCl$, $ZnCl_2$, $BiCl_3$, $Ti(OiPr)_4$ (OiPr=isopropoxide), rare earth heptafluorodimethyloctanedionates (=fod) and trifluoromethanesulfonates (=OTf), in particular, $Yb(fod)_3$, $Eu(fod)_3$, $Sc(OTf)_3$, $Yb(OTf)_3$, or of the ion exchangers, in particular, Amberlyst-15, or of the buffers, in particular, $Na_3PO_4/H_3PO_4$. The direct reaction is effected preferably using highly concentrated suspensions of monomeric glycosides, oligo- or polyglycosides in alcohols, preferably without addition of activators or homogeneous catalysts.

The equipment used in accordance with the invention is any suitable reactor having stirrers for the initial charging of the reaction partners, and a pump for the compression of the alcohols to or above the critical pressure. A suitable pump with suspension ball valves is supplied, for example, by LEWA. In order to ensure a reaction, both the critical temperature and the critical pressure of the alcohol have to be attained and preferably exceeded. In order to obtain a sufficient reaction rate, the critical parameters are preferably exceeded by from 5 to 15%. Table 1 lists some examples of critical parameters of alcohols. The reaction proceeds in a heatable reactor which may be operated continuously or batchwise.

TABLE 1

Critical data of selected reaction alcohols:

| Alcohols | $T_c$/K | $p_c$/bar |
|---|---|---|
| Methanol | 512.6 | 80.9 |
| Ethanol | 513.9 | 61.4 |
| n-Propanol | 536.8 | 51.7 |
| 2-Propanol | 508.4 | 47.6 |
| Butanol | 563.0 | 44.2 |
| Octanol | 625.5 | 28.6 |
| Hexadecanol | 770.0 | 16.1 |
| Octadecanol | 790.0 | 12.8 |
| Glycerol | 726.05 | 66.9 |

$T_c$ = critical temperature
$p_c$ = critical pressure

The apparatus used in accordance with the invention is shown schematically in the sole FIGURE of the present application. The reactants are initially charged in a suitable stirred vessel (A). From this reservoir, the mixture is conveyed by a suitable pump (B) into the reactor (C). The pump is capable of bringing the mixture to a pressure at or above the critical pressure of the alcohol of the formula (II) in A. The heater (D) is used to heat the reactor (C) to a temperature greater than or equal to the critical temperature of the alcohol. At the outlet of the reactor (C), a valve (E) can be used to regulate the pressure in the reaction setup. In addition, it is thus possible to adjust the residence times individually to the particular glycoside or the glycoside/poly-/oligoglycoside mixture, as a result of which degradation can be minimized. To minimize by-products, a carrier stream comprising pure alcohol from the reservoir (F) can be heated by means of the pump $B^1$ using the preheater (G) to a temperature of from 100° C. to 800° C., preferably at least to the critical temperature. At the mixing point (H), the carrier stream (CS) is mixed with the reactant stream (RS) and fed to the reactor. The ratio of CS/RS may lie within wide ranges of from 0/100 to 99/1, preferably from 20/80 to 80/20. When the preheating temperature selected is sufficiently high that a reaction temperature is already present at the mixing point, the temperature gradient in the reactor has to be adjusted to a sufficiently low level in order to prevent carbonization.

For the identification of the reaction products, especially GC, GC-MS, HPLC and MALDI have been found to be suitable analytical methods.

The following examples are provided to illustrate the method of the present invention.

EXAMPLES

In all examples, analysis was carried out immediately after the experiments by NMR and GC/MS. All examples were carried out in an apparatus according to the sole FIGURE provided in the present application. To convey the reaction mixtures, LEWA EK08 pumps with an HK 8 mm pump head were used.

Application Example 1

Preparation of Methylglucoside:

A mixture of methanol and glucose was initially charged in a stirred vessel A. The fraction of glucose was 30% of the methanol fraction. The mixture was conveyed by a suitable pump B at a pressure of 120 bar continuously through the reactor C. The tubular reactor C was heated to a temperature of 160° C. by the heater D. A carrier stream comprising pure methanol from the reservoir F was heated to approx. 300° using the preheater G. At the mixing point H, the carrier stream was mixed with the reactant stream and fed to the reactor. The preheating temperature was sufficiently high that reaction temperature was already present at the mixing point, so that the temperature gradient in the reactor was sufficiently low to prevent carbonization at the wall. The residence time in the tubular reactor was approx. 2 min. With the aid of the control valve E, the pressure was kept at the target value mentioned. At the outlet of the system, the reacted product mixture was collected. According to HPLC, the product mixture contained 3% product.

Application Example 2

Preparation of Methylfructoside:

A mixture of methanol and fructose was initially charged in a stirred vessel A. The fraction of fructose was 30% of the methanol fraction. The mixture was conveyed by a suitable pump B at a pressure of 120 bar continuously through the reactor C. The tubular reactor C was heated to a temperature of 160° C. by the heater D. A carrier stream comprising pure methanol from the reservoir F was heated to approx. 300° using the preheater G. At the mixing point H, the carrier stream was mixed with the reactant stream and fed to the reactor. The preheating temperature was sufficiently high that reaction temperature was already present at the mixing point, so that the temperature gradient in the reactor was sufficiently low to prevent carbonization at the wall. The residence time in the tubular reactor was approx. 2 min. With the aid of the control valve E, the pressure was kept at the target value mentioned. At the outlet of the system, the reacted product mixture was collected. According to HPLC, the product mixture contained 4% product.

Application Example 3

Preparation of Ethylglucoside:

A mixture of ethanol and glucose was initially charged in a stirred vessel A. The fraction of glucose was 30% of the ethanol fraction. The mixture was conveyed by a suitable pump B at a pressure of 120 bar continuously through the reactor C. The tubular reactor C was heated to a temperature of 150° C. by the heater D. A carrier stream comprising pure ethanol from the reservoir F was heated to approx. 280° C. using the preheater G. At the mixing point H, the carrier stream was mixed with the reactant stream and fed to the reactor. The preheating temperature was sufficiently high that reaction temperature was already present at the mixing point, so that the temperature gradient in the reactor was sufficiently low to prevent carbonization at the wall. The residence time in the tubular reactor was approx. 2 min. With the aid of the control valve E, the pressure was kept at the target value mentioned. At the outlet of the system, the reacted product mixture was collected. According to HPLC, the product mixture contained 10% product.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

We claim:

1. A process for preparing alkylpolyglycosides of glucose from glucose, oligo- or polyglycosides of glucose and alcohols according to the following reaction $$(Glyc\text{-}O)_z H + R^1 \text{---} OH \rightarrow (Glyc\text{-}O)_{z'} R^1$$

where
$z \geq 1$,
$z' \leq z$,
(Glyc-O)— is a glucose radical,
$R^1$ is a hydrocarbon radical which optionally contains multiple bonds and/or heteroatoms, the process comprising conducting the reaction at a temperature at or above the critical temperature and at or above the critical pressure of the alcohol.

2. The process as claimed in claim 1, wherein the critical pressures and critical temperatures are at least 5% above the critical parameters of the alcohols.

3. The process as claimed in claim 1, wherein the reaction is carried out continuously or batchwise and the reaction mixture has a residence time in the reactor of 1 s to 24 h.

4. The process as claimed in claim 3, wherein the residence time is from 1 s to 1 h.

5. The process as claimed in claim 4, wherein the residence time is from 1 s to 5 min.

6. The process as claimed in claim 1, wherein a carrier stream of the alcohol preheated to a temperature of from 100° C. to 800° C. is mixed with a reactant stream upstream of a reactor inlet.

7. The process as claimed in claim 1, wherein, in the formula $(Glyc\text{-}O)_z H$, $z>1$ and the formula represents oligo- or polyglycosides of glucose.

8. The process as claimed in claim 1, wherein the alcohol $R^1$—OH is at least one compound in which $R^1$ is a branched or unbranched hydrocarbon radical optionally containing double bonds and/or heteroatoms, or a hydroxyalkyl, alkyloxy radical having from 1 to 30 carbon atoms.

9. The process as claimed in claim 1, wherein the alcohol used is at least one compound selected from the group consisting of methanol, ethanol, propanol, isopropanol, butanol, hexanol, octanol, decanol, dodecanol, hexadecanol, octadecanol, glycol, glycerol, and propanediol.

10. The process according to claim 9, wherein the critical conditions are attained or exceeded at least for one of the alcohol components.

11. The process as claimed in claim 1, wherein the reaction is carried out in the presence of suitable homogeneous and heterogeneous catalysts selected from the group consisting of protic acids, protic acid salts, rare earth heptafluorodimethyloctanedionates, trifluoromethanesulfonates, ion exchangers and buffers.

12. The process as claimed in claim 1, wherein $(Glyc\text{-}O)_z H$ is glucose and $R^1$—OH is methanol.

13. The process according to claim 1, wherein Z' is 1 to 10.

14. The process according to claim 1, wherein the reaction is conducted in the absence of a protic acid catalyst.

15. A process for preparing alkylglucosides from glucose and alcohols according to the following reaction $$(Glyc\text{-}O)_z H + R^1 \text{---} OH \rightarrow (Glyc\text{-}O)_{z'} R^1$$

where
z and z' is 1,
(Glyc-O)— is a glucose radical,
$R^1$ is a hydrocarbon radical which optionally contains multiple bonds and/or heteroatoms, the process comprising conducting the reaction at a temperature at or above the critical temperature and at or above the critical pressure of the alcohol.

* * * * *